United States Patent [19]

Fujio et al.

[11] Patent Number: 5,578,471

[45] Date of Patent: * Nov. 26, 1996

[54] PROCESS FOR THE PREPARATION OF ASCORBIC ACID-2-PHOSPHATE

[75] Inventors: Tatsuro Fujio; Akihiko Maruyama, both of Kanagawa-ken, Japan

[73] Assignee: Kyowa Hakko Kogyo Kabushiki Kaisha, Tokyo, Japan

[*] Notice: The term of this patent shall not extend beyond the expiration date of Pat. No. 5,212,079.

[21] Appl. No.: 129,017

[22] Filed: Sep. 28, 1993

Related U.S. Application Data

[63] Continuation of Ser. No. 871,263, May 3, 1991, abandoned, which is a continuation of Ser. No. 132,299, Dec. 15, 1987, abandoned.

[30] Foreign Application Priority Data

Dec. 18, 1986 [JP] Japan .................................. 61-302409

[51] Int. Cl.$^6$ ........................................................ C12P 9/00
[52] U.S. Cl. .......................... 435/131; 435/194; 435/170; 549/222
[58] Field of Search .................................... 435/131, 194, 435/170; 549/222

[56] References Cited

U.S. PATENT DOCUMENTS 4,136,175  1/1979  Rideout et al. ........................... 435/92

OTHER PUBLICATIONS

J. Org. Chem., 47, 3453 (1982) 3453–3456.
Mitsugi et al. *Agr. Biol. Chem.* vol. 28, pp. 586–600, 1964.
Bergey's Manual of Systematic Bacteriology, vol. 1, Krieg et al, ed. 1984, pp. 359–360.
ATCC Catalogue of Bacteria, 1989, pp. 11, 111, 433.
Enzyme Nomenclature 1978, Academic Press pp. 207–211.
Lehninger, *Principles of Biochemistry*, 1982 pp. 404, 415 and 458.

*Primary Examiner*—Irene Marx
*Attorney, Agent, or Firm*—Schweitzer Cornman & Gross

[57] ABSTRACT

The invention relates to a process for the preparation of ascorbic acid-2-phosphate, which comprises reacting ascorbic acid or araboascorbic acid with ATP to produce ascorbic acid-2-phosphate in an aqueous medium in the presence of an effective amount of an enzyme derived from a microorganism and capable of catalyzing the enzymatic reaction of ascorbic acid or araboascorbic acid with ATP to produce ascorbic acid-2-phosphate and recovering the resultant ascorbic acid-2-phosphate from the reaction solution.

7 Claims, 3 Drawing Sheets

PROCESS FOR THE PREPARATION OF ASCORBIC ACID-2-PHOSPHATE

This is a continuing application of U.S. Ser. No. 871,263, filed on May 3, 1991, now abandoned, which is a continuing application of U.S. Ser. No. 132,299, filed on Dec. 15, 1987, now abandoned.

The present invention relates to a process for the preparation of ascorbic acid-2-phosphate (hereinafter referred to as AsA2P). Ascorbic acid is widely used, for example, in the fields of medicines, foodstuffs and cosmetics but has the disadvantage that it is susceptible to decomposition, for example, by exposure to heat, air or light. AsA2P is a stable derivative which is easily converted into ascorbic acid by dephosphorylation in the body and hence exhibits vitamin C activity. AsA2P is therefore widely used, for example, as a raw material for the preparation of cosmetics and medicines, particularly cosmetics, and as an additive to foodstuffs.

Processes for the preparation of AsA2P by chemical synthesis are known [for example, JP-A-30328/70, 15605/73 and 18191/77 and J. Org. Chem. 47, 3453 (1982)]. However, the preparation of AsA2P using a microbiological process has not previously been reported.

Chemical synthesis has already been used for the preparation of AsA2P on an industrial scale. However, chemical synthesis has the inherent disadvantage that, in addition to the desired phosphorylation at the 2-position, for example, various isomers phosphorylated at the 3- and 5-positions may be produced and thus it is difficult to obtain a high yield of AsA2P. Consequently, various attempts have been made to improve the production yield of AsA2P, for example, by introducing a protecting group or by selecting the operation conditions. However, using the known processes the preparations are still complicated and expensive and, moreover, it is difficult to produce AsA2P with high purity.

The present inventors have discovered that certain microorganisms are capable of specifically phosphorylating the 2-position of ascorbic acid and araboascorbic acid and have found microorganisms capable of producing AsA2P from ascorbic acid or araboascorbic acid and adenosine triphosphate (ATP). The present invention therefore provides an alternative process for the preparation of AsA2P on an industrial scale.

The present invention will be explained in detail in the following specification.

According to the present invention there is provided a process for the preparation of ascorbic acid-2-phosphate, which comprises reacting ascorbic acid or araboascorbic acid with ATP to produce ascorbic acid-2-phosphate in an aqueous medium in the presence of an effective amount of an enzyme derived from a microorganism and capable of catalizing the enzymatic reaction of ascorbic acid or araboascorbic acid with ATP to produce ascorbic acid-2-phosphate and recovering the resultant ascorbic acid-2-phosphate from the reaction solution.

It will be understood that the term ascorbic acid includes both D- and L-isomeric forms of ascorbic acid.

The microorganisms which may be used for the purpose of the present invention include those capable of producing AsA2P from ascorbic acid or araboascorbic acid and ATP and belonging to the genus Aeromonas, Klebsiella, Flavobacterium, Pseudomonas, Bacillus or Beneckea and are preferably exemplified by

| | |
|---|---|
| *Aeromonas caviae* | ATCC 13137 |
| *Bacillus subtilis* | ATCC 19221 |
| *Beneckea hyperoptica* | ATCC 15803 |
| *Flavobacterium devorans* | ATCC 10829 |
| *Klebsiella oxytoca* | ATCC 8724 |
| *Pseudomonas azotocolligans* | ATCC 12417 |
| *Pseudomonas chlororaphis* | ATCC 9446 | and mutants thereof.

It is possible to culture the microorganisms using conventional media, for example, KM102 medium containing polypeptone (10 g/l), meat extract (7 g/l), yeast extract (5 g/l) and sodium chloride (3 g/l) and having an adjusted pH of 7.2, provided the microorganisms used are capable of growing well without inhibition of their ability to produce AsA2P. It is also possible to use various organic, semi-synthetic and synthetic media containing sources of carbon, nitrogen and other inorganic and/or organic substances.

Preferred carbon sources include, for example, carbohydrates such as glucose, fructose, sucrose or maltose; sugar alcohols such as mannitol or sorbitol; alcohols such as glycerol; organic acids such as pyruvic acid, lactic acid or citric acid; and amino acids such as glutamic acid, methionine or lysine. If desired, other naturally-occurring organic nutrients such as starch hydrolyzate, molasses, waste molasses, white rice bran, cassava, bagasse or corn steep liquor may be used.

Examples of nitrogen sources include inorganic and organic ammonium salts such as urea, ammonia, ammonium chloride, ammonium sulfate, ammonium carbonate, or ammonium acetate; amino acids such as glutamic acid, glutamine or methionine; and nitrogen-containing organic materials such as peptone, NZ amine, corn steep liquor, meat extract, yeast extract, casein hydrolyzate, fish meal and digested products thereof or chrysalis hydrolyzate.

Examples of inorganic substances include dibasic potassium phosphate, monobasic sodium phosphate, magnesium sulfate, sodium chloride, calcium chloride, iron chloride, copper sulfate, manganese chloride, ammonium molybdate and zinc sulfate, of which suitable amount may be added to the medium.

Vitamins, amino acids, nucleic acids and other substances which may be required for the growth of the microorganism may, if desired, be added to the medium.

It is preferred to carry out the culturing under aerobic conditions, for example, with shaking or with aeration and agitation. Usually the culturing may be effected at a temperature of from 20° to 40° C., preferably from 25° to 35° C. and at a pH of from 5 to 10, preferably from 6.5 to 7.5 for a period of 10 to 100 hours.

AsA2P is formed by the reaction of ascorbic acid or araboascorbic acid with ATP which may be carried out by either of the following two methods: (1) combining ascorbic acid or araboascorbic acid with ATP in the culture broth of a microorganism; or (2) mixing at least one member selected from concentrated culture broth, dried culture broth, supernatant of a culture broth, microbial cells and products oftained by treatment thereof, such as freeze-thawed cells, freeze-dried cells, immobilised enzym and enzyme extracted from microbial celles (either from a native microbial stain or from a suitable genetically engineered strain), with a solution containing ascorbic acid or araboascorbic acid and ATP.

Additives such as surfactants or organic solvents may, if desired, be added to the reaction solution to increase the production yield of AsA2P.

Suitable surfactants include cationic surfactants such as polyoxyethylene stearylamine (for example, Nymin S-215, commercial product of Nihon Yushi K. K., Japan) or cetyltrimethylammonium bromide; anionic surfactants such as sodium oleylamide sulfate; and amphoteric surfactants such as polyoxyethylenesorbitan monostearate (for example, Nonion ST 221, commercial product of Nihon Yushi K. K., Japan), which are capable of promoting the reaction to produce AsA2P from ascorbic acid or araboascorbic acid and ATP. Usually, the surfactant may be used in an amount of from 1 to 50 mg/ml, preferably from 1 to 20 mg/ml.

Examples of suitable organic solvents include toluene, xylene, acetone, aliphatic alcohols, benzene, and ethyl acetate, which may usually be used in an amount of from 0.1 to 50 µl/ml, preferably from 1 to 20 µl/ml. It is also possible to use magnesium ions at a concentration of from 1 to 100 mM.

Both chemically pure and crude ascorbic acid or araboascorbic acid and ATP may be used for the purpose of the invention insofar as they contain ascorbic acid or araboascorbic acid or ATP and are not detrimental to AsA2P formation.

It is preferred to use ascorbic acid or arabo-ascorbic acid and ATP at concentrations of from 1 to 500 mM and from 1 to 1000 mM respectively.

In the second method, it is preferred to carry out the reaction at a temperature of from 20° to 70° C. for a period of 1 to 48 hours, the pH being kept at 3 to 11 by the addition of, for example, ammonia, NaOH or KOH.

Examples of the products obtained by treatment of the culture broth include concentrated or dried culture broth, products obtained by adding a surfactant and/or organic solvent to the culture broth, products obtained by treating the cells with bacteriolytic enzyme, immobilized microbial cells and enzyme products extracted from the microbial cells.

The cells separated from the culture broth may preferably be used in an amount of from 1 to 400 mg/ml (wet cell weight).

It is possible to determine AsA2P quantitatively by measuring the absorption at 254 nm following high performance liquid chromatography through a Nucleosil 10 $C_{18}$ column (commercial product of Masnerey-Nagel, Germany) using a pure preparation of AsA2P obtained by chemical synthesis as a reference.

Isolation of AsA2P from the culture broth or the reaction solution may be effected by removing the cells from the culture broth where necessary, removing proteins from the supernatant, neutralizing said supernatant and subsequently purifying the solution by column chromatography using, for example, ion-exchange resins, Sephadex or high performance liquid chromatography.

The following non-limiting examples illustrate the present invention.

EXAMPLE 1

Figure 1B:
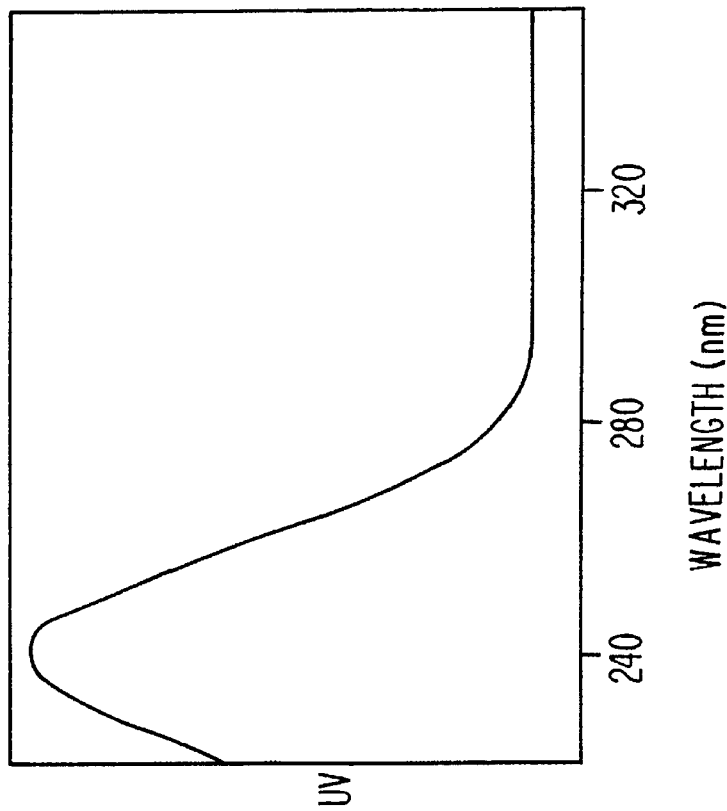
FIGS. 1 A and B show the ultraviolet absorption spectra of a reference AsA2P and AsA2P prepared by the process of Example 1 (RCI) respectively.

*Flavobacterium devorans* ATCC 10829 was cultured in KM102 medium (30 ml) at a temperature of 30° C. for 20 hours in an Erlenmeyer flask (capacity 300 ml) to obtain a seed. The (12 ml) was then transferred to KM102 medium (300 ml) in an Erlenmeyer flask (capacity 2 l) for culturing at a temperature of 30° C. for 20 hours. Wet cells (5.4 g) were obtained by centrifugation (10,000×g/10 min) of the resultant culture broth. The wet cells were frozen and preserved at a temperature of −20° C. A reaction solution (50 ml) composed of ascorbic acid (30 mM), ATP (40 mM), $MgSO_4$ (10 mM) and $KH_2PO_4$ (40 mM) and containing the preserved cells (50 mg/ml wet weight) was stirred with a magnetic stirrer (100 r.p.m.) in a beaker (capacity 200 ml) for 24 hours at 30° C. to complete the reaction, whilst the pH was adjusted to about 6.5 using caustic soda.

The supernatant of the culture broth following the reaction contained 1.16 mg/ml of AsA2P and by-products such as ascorbic acid-5-phosphate and ascorbic acid-3-phosphate were substantially absent.

After adjusting the pH of the reaction solution to 3.0 with hydrochloric acid, the solution (50 ml) was centrifuged to remove proteins. The supernatant was neutralized with caustic soda and passed through a column packed with 300 ml of Dowex 1×8 resin (Cl form) followed by concentration gradient elution using 0.2–0.6M $NaHCO_3$. The resultant fractions containing AsA2P were collected, combined and neutralized with hydrochloric acid, followed by concentration. The resultant fraction (163 ml) contained 42 mg of AsA2P. The concentrate was then passed through a column packed with Sephadex G-10 (500 ml) to obtain a fraction (63 ml) containing 30 mg of AsA2P which showed a single peak by high performance liquid chromatography. The resultant sample designated RCI was used for analysis of the chemical structure as described hereinafter.

(1) Ultraviolet Ray Absorption Spectra

Figure 1A:
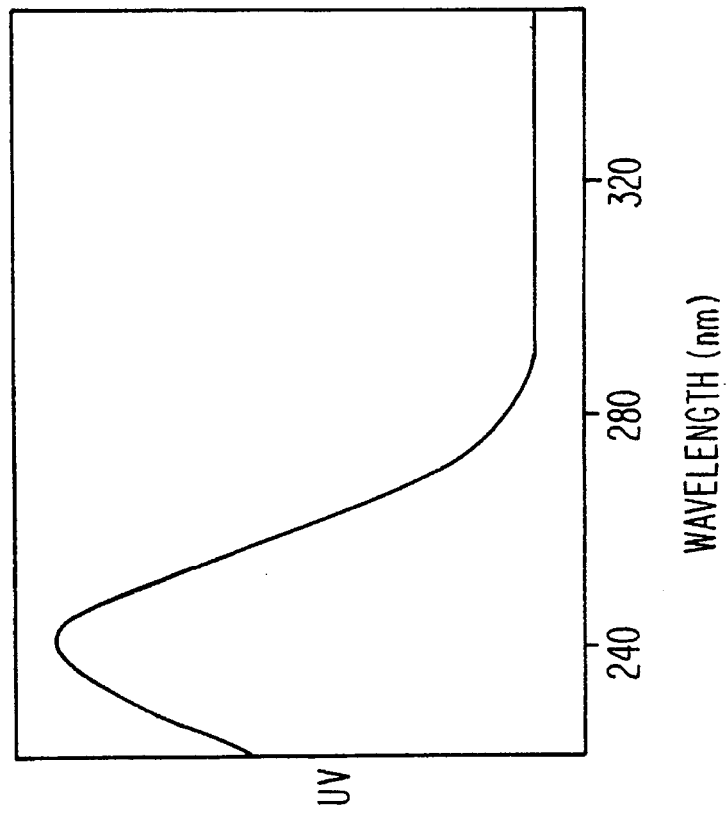

FIG. 1 (A) and (B) show respectively the ultraviolet ray absorption spectra of the reference AsA2P and the sample RCI. It was noted that RCI had a maximum absorption at 240 nm and its pattern was completely identical with the pattern of the reference AsA2P.

(2) Cleavage With Alkaline Phosphatase

15 µl of RCI (25 mg/ml) was added to a solution composed of 0.5M glycine-buffered solution (pH 10.5; 20 µl), 0.1M $ZnSO_4$ (1 µl), 0.1M $MnSO_4$ (1 µl), 2 µl alkaline phosphatase (containing 20 mg/ml of the enzyme; commercial product of Sigma) and deionized water (36 µl). The solution was kept at a temperature of 37° C. for 30 minutes to observe the degree of enzymatic decomposition of RCI.

The following Table 1 shows the results from the analysis of the supernatant by high performance liquid chromatography.

TABLE 1

| Sample | Concentration (mM) | | |
|---|---|---|---|
| | AsA2P | AsA | Pi** |
| I Reaction product | | | |
| Before reaction | 14.5 | 0 | 3.5 |
| After reaction | 0.9 | 12.5 | 14.5 |
| Control* | 13.4 | 0 | 4.3 |
| II Reference | | | |
| Before reaction | 14.4 | 0 | 1.5 |
| After reaction | 1.1 | 12.2 | 14.0 |
| Control* | 14.0 | 0 | 2.1 |

Note:
*Containing deionized water instead of alkaline phosphatase
**Inorganic phosphate This table indicates that RCI represents ascorbic acid which has been phosphorylated.

(3) Analysis by Proton-NMR

Figure 2A:
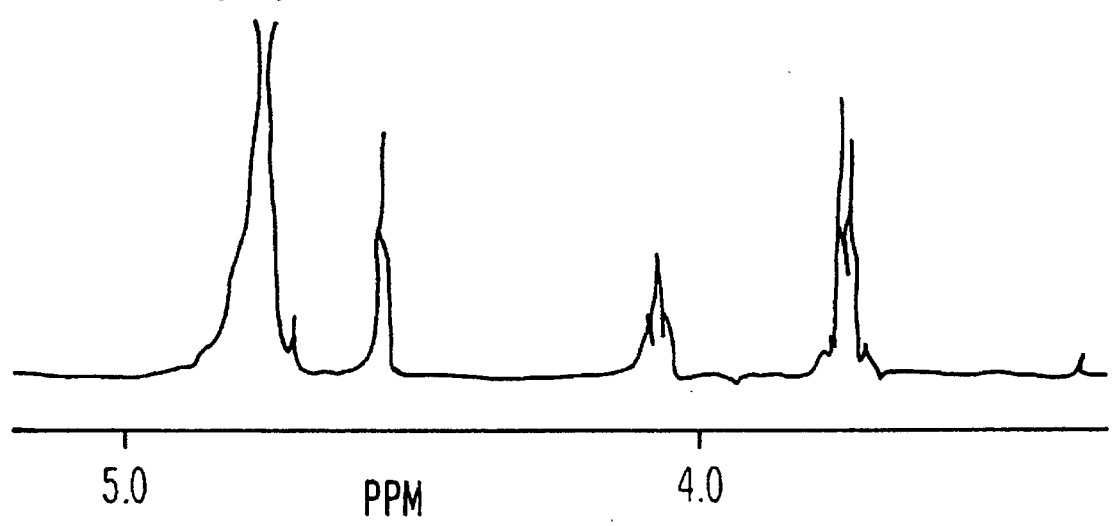
FIGS. 2 A, B and C show the results from proton-NMR of the reference AsA2P, AsA2P prepared by the process of Example 1 (RCI) and a mixture of the reference AsA2P and RCI respectively.
Figure 2B:
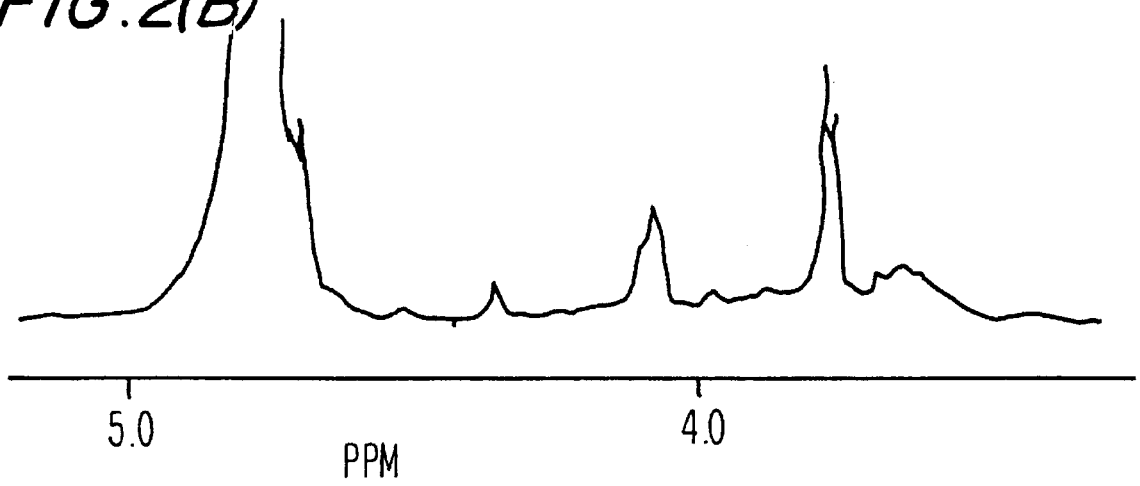
Figure 2C:
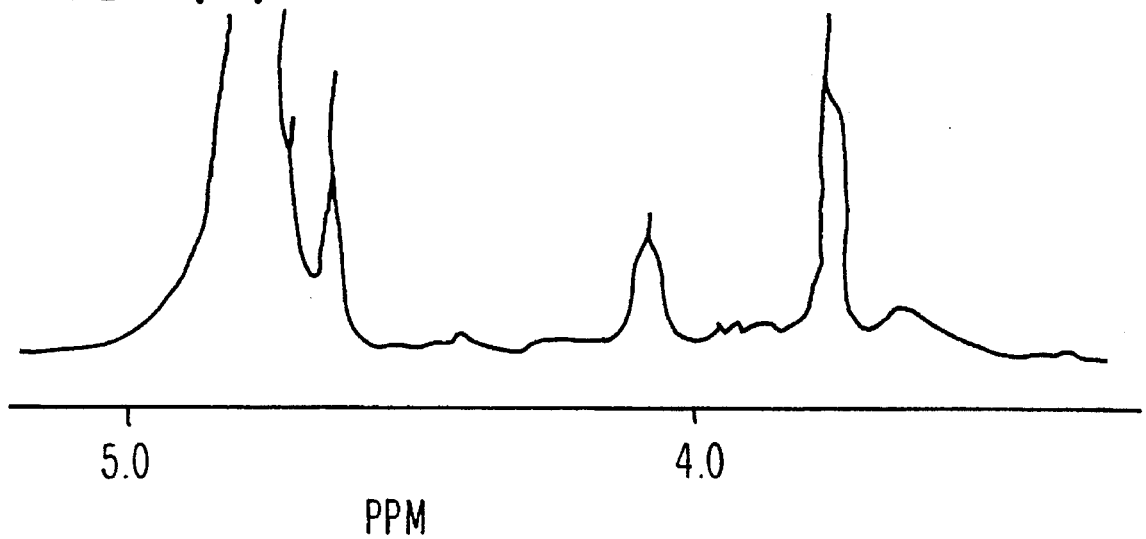

FIG. 2 (A), (B) and (C) show respectively the patterns of proton-NMR spectra of the reference AsA2P, RCI and a mixture of the reference AsA2P with RCI, from which it was noted that RCI was identical with the reference AsA2P.

(4) Analysis by $^{13}$C-NMR

Figure 3A:
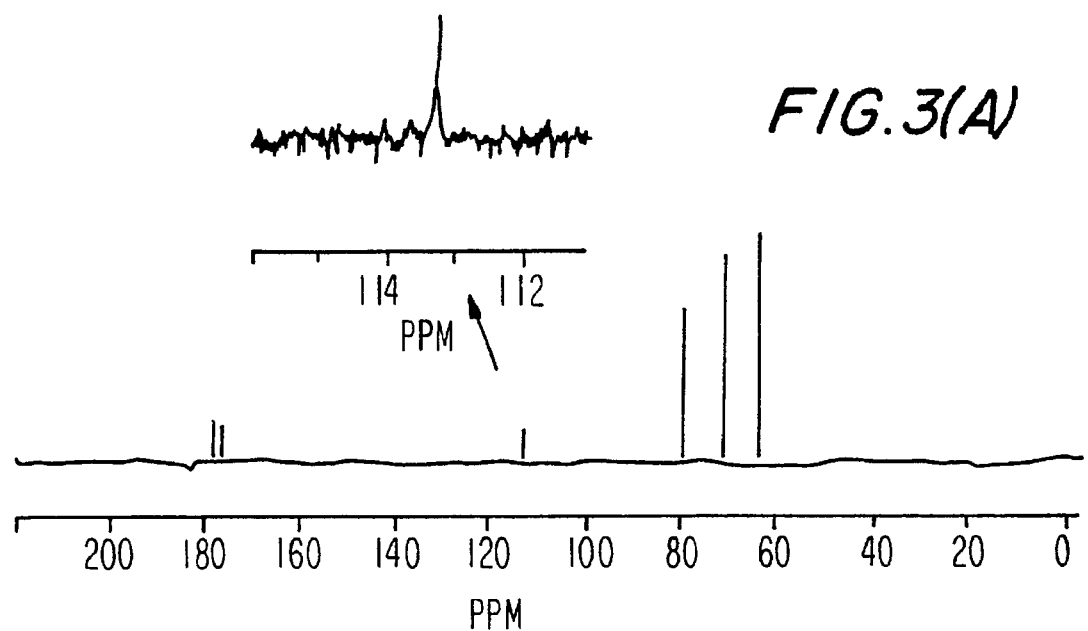
FIGS. 3 A and B show the results from $^{13}$C-NMR of the reference AsA2P and RCI.
Figure 3B:
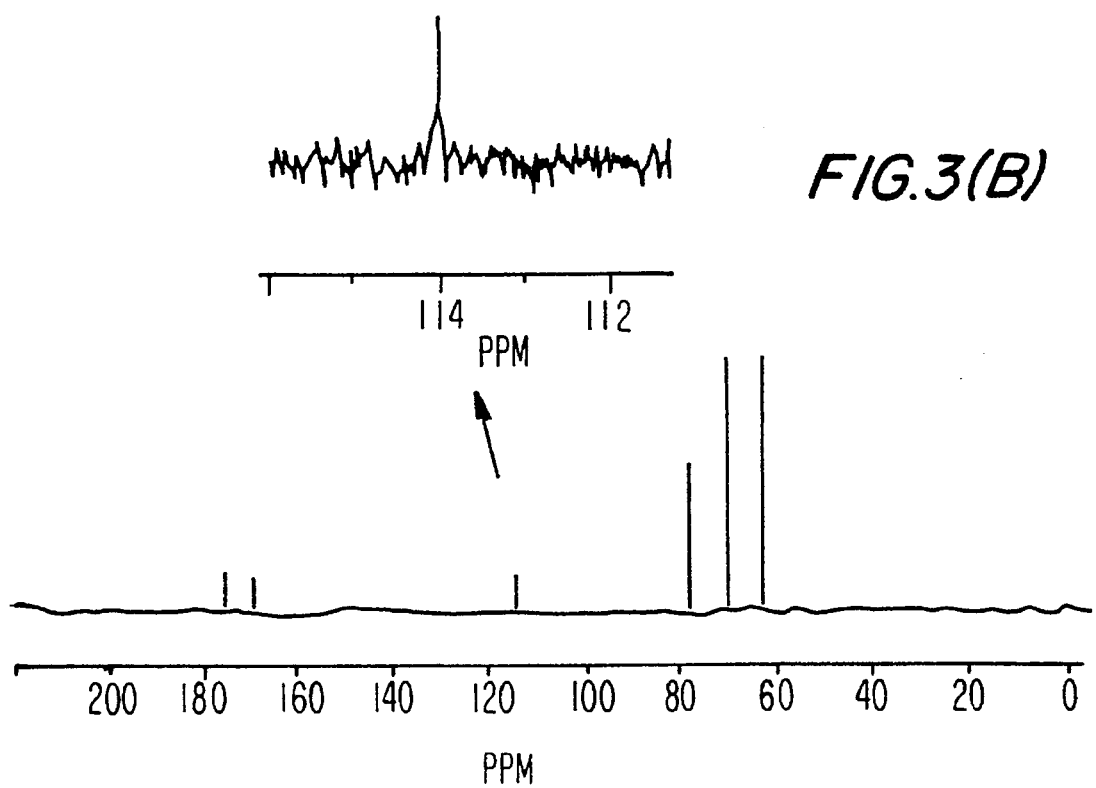

FIG. 3 (A) and (B) show respectively the patterns of $^{13}$C-NMR spectra of RCI and the reference AsA2P, both of which indicate that the carbon atom at the 2-position of each sample has been phosphorylated. Thus it is apparent that RCI is identical with the reference AsA2P.

EXAMPLE 2

Each strain shown in Table 2 was cultured in KM102 medium (30 ml) at a temperature of 30° C. for 20 hours in an Erlenmeyer flask (capacity 300 ml). The resultant seed (12 ml) was transferred to KM102 medium (300 ml) in an Erlenmeyer flask (capacity 2 l) for culturing at a temperature of 30° C. for 20 hours. The culture broth thus-obtained was centrifuged (10,000×g/10 min) and the microbial cells were frozen and preserved at a temperature of −20° C. Subsequently, a reaction solution (50 ml) composed of the frozen cells (50 mg/ml), ascorbic acid (30 mM), ATP (40 mM), MgSO$_4$ (10 mM) and KH$_2$PO$_4$ (40 mM) in a beaker (capacity 200 ml) was stirred (100 r.p.m.) with a magnetic stirrer at 30° C. for 24 hours, whilst the pH was adjusted to about 6.5 with caustic soda. After completion of the reaction, the resultant concentration of AsA2P in the supernatant of the reaction solution was determined by high performance liquid chromatography. The results are shown in Table 2.

TABLE 2

| Microorganism | | AsA2P (mg/ml) |
|---|---|---|
| Aeromonas caviae | ATCC 13137 | 0.36 |
| Bacillus subtilis | ATCC 19221 | 0.22 |
| Beneckea hyperoptica | ATCC 15803 | 0.35 |
| Klebsiella oxytoca | ATCC 8724 | 0.26 |
| Pseudomonas azotocolligans | ATCC 12417 | 0.33 |
| Pseudomonas chlororaphis | ATCC 9446 | 0.21 |

EXAMPLE 3

Pseudomonas azotocolligans ATCC 12417 was cultured in KM102 medium (30 ml) at a temperature of 30° C. for 20 hours in an Erlenmeyer flask (capacity 300 ml). The resultant seed (12 ml) was cultured in KM102 medium (300 ml) at a temperature of 30° C. for 20 hours in an Erlenmeyer flask (capacity 2 l). The culture broth was centrifuged (10,000×g/10 min) to separate the cells. The cells were divided into fractions which were then separately subjected to different treatments such as:
(a) no treatment;
(b) air-drying;
(c) freezing at a temperature of −20° C., followed by defrosting;
(d) suspending in a solution containing a surfactant;
(e) suspending in a solution containing an organic solvent;
(f) suspending in a solution containing a mixture of a surfactant and an organic solvent; or
(g) treating with ultrasonic waves.

The AsA2P-producing activity of each sample was determined in the following manner:

A reaction solution (50 ml) composed of cells treated as above (50 mg/ml), ascorbic acid (30 mM), ATP (40 mM), MgSO$_4$ (10 mM) and KH$_2$PO$_4$ (40 mM) was stirred (100 r.p.m.) with a magnetic stirrer in a beaker (capacity 200 ml) for a period of 24 hours at 30° C., whilst the solution was adjusted to a pH of about 6.5 with caustic soda. High performance liquid chromatography was used to determine the concentration of AsA2P present in the supernatant of the culture broth and the results are shown in Table 3.

TABLE 3

| Enzyme source | AsA2P (mg/ml) |
|---|---|
| Untreated cells | 0.056 |
| Air-dried cells | 0.121 |
| Freeze-dried cells | 0.350 |
| Added P* (4 mg/ml) | 0.214 |
| Added X** (10 ml/l) | 0.211 |
| Added P* (4 mg/ml) and X** (10 ml/l) | 0.252 |
| Treated with ultrasonic waves | 0.327 |

Notes:-
*Polyoxyethylene stearylamine (Nymin S-215, commercial product of Nihon Yushi K.K., Japan
**Xylene The Ultrasonic breaker used in Example 4 was used at an output nambered as "5" to apply ultrasonic waves at unknown KHz 6 times (each for 30 seconds with an interval of 30 seconds).

EXAMPLE 4

Flavobacterium devorans ATCC 10829 was cultured in a similar manner to that described in Example 1. The resultant microbial cells were centrifuged and resuspended in a phosphate-buffered solution (pH 7.0) at a concentration of 200 mg/ml. The cell suspension was intermittently treated for 10 minutes with an ultrasonic wave breaker (UR-200P, commercial product of Tomy Seiko K. K., Japan) to disrupt the cells. The cells were divided into fractions and each fraction was subjected to one of the following different treatments
(1) the culture broth without any after-treatment;
(2) the solution of broken cells or
(3) the supernatant resulting from centrifugation of the broken cells (12,000×g/15 min).

On each occasion, the resultant material was then subjected to the reaction in a similar manner to that described in Example 1. It was noted that 0.102 mg/ml, 0.175 mg/ml and 0.168 mg/ml of AsA2P were formed and accumulated respectively using samples (1), (2) and (3).

EXAMPLE 5

Flavobacterium devorans ATCC 10829 was cultured in a similar manner to that described in Example 1. To the resultant culture broth were added L-ascorbic acid (30 mM), ATP (40 mM), MgSO$_4$ (10 mM) and KH$_2$PO$_4$ (40 mM) to prepare a reaction solution which was then stirred (100 r.p.m.) for 20 hours at 30° C. with a magnetic stirrer, whilst the pH was adjusted to 6.5 with caustic soda. It was noted that 0.131 mg/ml of AsA2P was formed and accumulated in the supernatant of the reaction mixture at the time of completion of the reaction.

EXAMPLE 6

Flavobacterium devorans ATCC 10829 was cultured in a similar manner to that described in Example 1. The culture broth was centrifuged (10,000×g/10 min) to obtain wet cells (5.4 g) which were then frozen at −20° C. and preserved. A reaction solution composed of araboascorbic acid (30 mM), ATP (40 mM), MgSO$_4$ (10 mM) and KH$_2$PO$_4$ (40 mM) and containing 50 mg/ml (wet cell weight) of the preserved cells was put into a 200 ml beaker and stirred (100 r.p.m./24 hours) with a magnetic stirrer. The pH was adjusted to 6.5 with intermittent addition of caustic soda solution during the reaction. 0.87 mg/ml of AsA2P was accumulated in the reaction mixture. Substantially no by-products such as ascorbic acid-5-phosphate, ascorbic acid-3-phosphate and pyrophosphoric compounds of ascorbic acid were detected.

The present invention provides a process for the preparation of AsA2P from ascorbic acid or araboascorbic acid and ATP by the use as a source of enzyme at least one member selected from microbial cells, the culture broth of microorganisms, the supernatant of the culture broth, and products from the microbial cells.

We claim:

1. A process for the preparation of ascorbic acid-2-phosphate, which comprises the steps of:

reacting ascorbic acid with ATP in an aqueous medium in with a microorganism selected from the group consisting of

| | |
|---|---|
| *Aeromonas cavias* | ATCC 13137 |
| *Bacillus subtilis* | ATCC 19221 |
| *Baneckea hyperoptica* | ATCC 15803 |
| *Flavobacterium devorans* | ATCC 10829 |
| *Klebsiella oxytoca* | ATCC 8724 |
| *Pseudomonas azotocolligans* | ATCC 12417 and |
| *Pseudomonas chloroaphis* | ATCC 9446, | said microorganism being capable of catalyzing the enzymatic reaction of ascorbic acid with ATP to produce ascorbic acid-2-phosphate; and recovering the resultant ascorbic acid-2-phosphate from the reaction solution.

2. A process according to claim 1, wherein the microorganism used is *Flavobacterium devorans* ATCC 10829, or *Pseudomonas azotocolligans* ATCC 12417.

3. A process according to claim 1, wherein the enzymatic reaction is effected in a culture broth of said microorganism.

4. The process according to claim 3, wherein said reacting step further comprises maintaining said culture broth at a temperature of from 20 to 40 degrees C. and at a pH of from 5 to 10 for a period of 10 to 100 hours.

5. A process according to claim 1, wherein the enzymatic reaction is effected by placing ascorbic acid in contact with ATP in the presence of at least one microorganism source selected from the group consisting of concentrated culture broth of said microorganism, dried culture broth of said microorganism, supernatant of a culture broth of said microorganism, and microbial cells of said microorganism.

6. A process according to claim 5, wherein the reaction is effected at a temperature of from 20 to 70 degrees C. and at a pH of from 3–11 for a period of 1–48 hours.

7. The process of claim 1, wherein said microorganism is *Pseudomonas azotocolligans* ATCC 12417.

* * * * *